US010473626B2

(12) United States Patent
Leach et al.

(10) Patent No.: US 10,473,626 B2
(45) Date of Patent: Nov. 12, 2019

(54) METHOD FOR THE GRAPHICAL REPRESENTATION AND DATA PRESENTATION OF WELD INSPECTION RESULTS

(71) Applicant: Loenbro Inspection, LLC., Black Eagle, MT (US)

(72) Inventors: Jeffrey Benjamin Leach, Gladstone, OR (US); Parrish Alan Furr, Trussville, AL (US)

(73) Assignee: Loenbro Inspection, LLC., Black Eagle, MT (US)

( * ) Notice: Subject to any disclaimer, the term of this patent is extended or adjusted under 35 U.S.C. 154(b) by 385 days.

(21) Appl. No.: 15/480,077

(22) Filed: Apr. 5, 2017

(65) Prior Publication Data

US 2018/0292357 A1 Oct. 11, 2018

(51) Int. Cl.
*B23K 31/00* (2006.01)
*B23K 31/12* (2006.01)
(Continued)

(52) U.S. Cl.
CPC ....... *G01N 29/069* (2013.01); *G01N 29/0672* (2013.01); *G01N 29/262* (2013.01);
(Continued)

(58) Field of Classification Search
CPC ............... G01N 29/262; G01N 29/043; G01N 2291/106; G01N 2291/044; G01N 29/11; G01N 2291/267; G01N 29/265; G01N 2291/2638; G01N 29/28; G01N 29/0645; G01N 29/225; G01N 2291/2675; G01N 2291/0231; G01N 2291/2634; G01N 2291/2672; G01N 29/04; G01N 2291/0258; G01N 2291/02854; G01N 2291/0289; G01N 2291/056; G01N 29/069;
(Continued)

(56) References Cited

U.S. PATENT DOCUMENTS 6,532,820 B1 * 3/2003 Fleming ............ G01N 29/0609
73/620
8,250,923 B2 * 8/2012 Ehara ..................... G01N 29/07
376/252

(Continued)

*Primary Examiner* — Erin B Saad
(74) *Attorney, Agent, or Firm* — Haynes and Boone, LLP

(57) ABSTRACT

A system and method directed to displaying images and presenting the data from the phased array ultrasonic testing (PAUT) inspection of a plurality of welded joints within a welded object. The system includes an engine comprising memory, a graphical user interface (GUI), an export module, a transformation module, and a merger module each operably coupled to one another. The export module is used to extract images and data from the PAUT inspection of the welded joints. The exported information is used by the transformation module to create a multi-dimensional representation of the PAUT inspected welded joint for each joint. The merger module combines the information from the export module and the transformation module into an evaluation report for each PAUT inspected welded joint and assembles the evaluation report into a master report for analysis. The system may be communicatively coupled over a network using a network interface.

18 Claims, 9 Drawing Sheets

(51) Int. Cl.
*G01N 29/00* (2006.01)
*G01N 29/06* (2006.01)
*G01N 29/26* (2006.01)

(52) U.S. Cl.
CPC .... *B23K 31/125* (2013.01); *G01N 2291/0234* (2013.01); *G01N 2291/0289* (2013.01); *G01N 2291/267* (2013.01)

(58) Field of Classification Search
CPC ...... G01N 29/07; G01N 29/223; G01N 29/24; G01N 29/2487; G01N 29/30; G01N 2291/015; G01N 2291/0234; G01N 2291/0235; G01N 2291/0421; G01N 2291/0422; G01N 2291/101; G01N 2291/105; G01N 2291/2632; G01N 2291/2636; G01N 27/82; G01N 27/85; G01N 29/06; G01N 29/0609; G01N 29/221; G01N 29/4445; G01N 2291/023; G01N 2291/02818; G01N 2291/02836; G01N 2291/02863; G01N 2291/02881; G01N 2291/0423; G01N 2291/0427; G01N 2291/0428; G01N 2291/048; G01N 2291/2694; G01N 2291/2695; G01N 27/902; G01N 29/024; G01N 29/041; G01N 29/0618; G01N 29/0654; G01N 29/0663; G01N 29/14; G01N 29/226; G01N 29/2412; G01N 29/2462; G01N 29/2493; G01N 29/275; G01N 29/44; G01N 29/4409; G01N 29/4418; G01N 29/4463; G01N 29/4472; G01N 29/4481; B23K 31/003; B23K 31/125; B23K 31/12
See application file for complete search history.

(56) References Cited

U.S. PATENT DOCUMENTS

| | | | |
|---|---|---|---|
| 9,037,419 B2* | 5/2015 | Na | G01N 29/0645 |
| | | | 702/39 |
| 9,625,424 B2* | 4/2017 | LePage | G01N 29/262 |
| 10,113,993 B2* | 10/2018 | Spencer | G01N 29/043 |
| 10,324,066 B1* | 6/2019 | Davis | G01N 29/043 |
| 2013/0308419 A1* | 11/2013 | Singh | G01N 29/043 |
| | | | 367/7 |
| 2015/0253288 A1* | 9/2015 | Spencer | G01N 29/24 |
| | | | 73/602 |
| 2015/0346164 A1* | 12/2015 | St-Laurent | G01N 29/24 |
| | | | 73/588 |
| 2016/0370303 A1* | 12/2016 | Schmitz | G01N 23/083 |
| 2018/0231508 A1* | 8/2018 | Lepage | G01N 29/30 |
| 2018/0259489 A1* | 9/2018 | Bruch | G01N 29/0645 |
| 2018/0292357 A1* | 10/2018 | Leach | G01N 29/069 |

\* cited by examiner

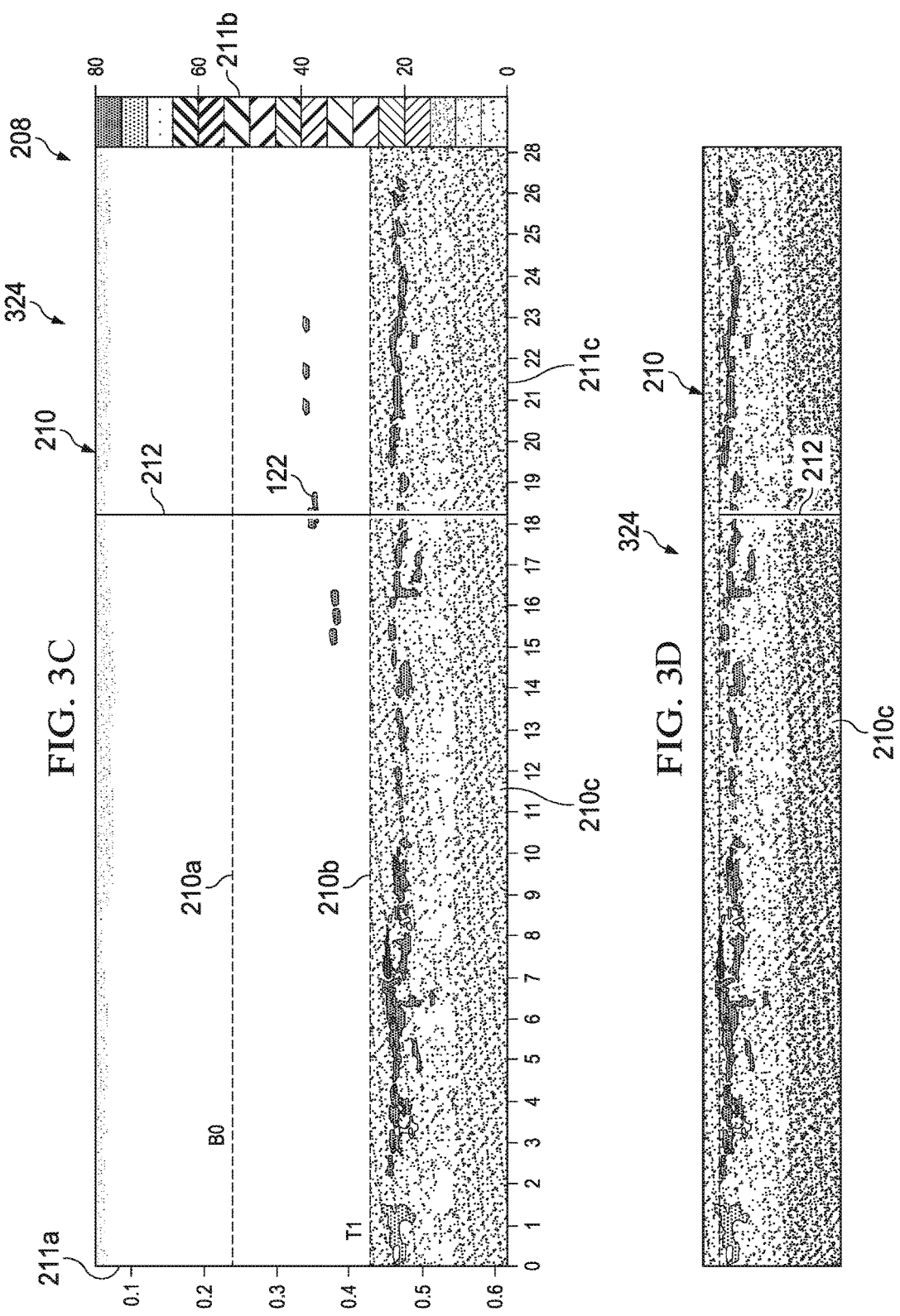

METHOD FOR THE GRAPHICAL REPRESENTATION AND DATA PRESENTATION OF WELD INSPECTION RESULTS

FIELD OF THE DISCLOSURE

The present disclosure relates generally to weld inspection, and more specifically, to inspection of welds associated with an object. More particularly still, the present disclosure relates to systems and methods for displaying images and presenting data obtained from the phased array ultrasonic testing inspection of a plurality of welds associated with a welded object.

BACKGROUND

Non-destructive testing (NDT) is a common method of testing the integrity of a welded joint within a welded object. In some forms of NDT, energy propagated into a welded object yields a signal that can be displayed as a waveform image. This waveform image can be instructive of the condition of the welded joint. Such propagated energy may be in the form of electromagnetic waves or acoustic waves. One common form of NDT using acoustic waves is phased array ultrasonic testing (PAUT). To inspect a welded joint by PAUT, a transducer and a wedge may be used to propagate acoustical signals towards a welded plane of a welded joint at various angles and patterns. Upon encountering the welded plane, if a discontinuity is present, the acoustical signals are reflected back towards the transducer where they are converted to electronic-amplitude signals and transmitted to a phased array testing instrument (PATI). The PATI generates a display of the reflected acoustical signals in various forms on ultrasound graphs. The displays and data represented thereby are not intuitive and comprehending the displays and data can be difficult for those not familiar with interpreting the results of ultrasonic testing.

In addition to the ultrasound graphs generated from the PAUT inspection, characteristics related to the welded object, the welded joint and the equipment used during the PAUT inspection are normally captured for evaluation. In the prior art, software programs are able to generate a report containing this information for only a single weld. However, many times, a welded object may have a plurality of welded joints which require integrity testing. Depending on the relative size of the welded object, there may be tens or even hundreds of welded joints that need to be inspected. Given the potential volume of welded joints within a welded object, inspecting such joints individually using conventional solutions may be a very tedious and time-consuming process.

BRIEF DESCRIPTION OF THE DRAWINGS

FIG. 3C depicts an enlarged view of an ultrasound B-scan image taken from a plurality of ultrasound images generated from the PAUT inspection of a welded joint, according to one or more illustrative embodiments.

FIG. 3D depicts an enlarged view of a reflection taken from the B-scan image of FIG. 3C, according to one or more illustrative embodiments.

DESCRIPTION OF ILLUSTRATIVE EMBODIMENTS

Figure 1:
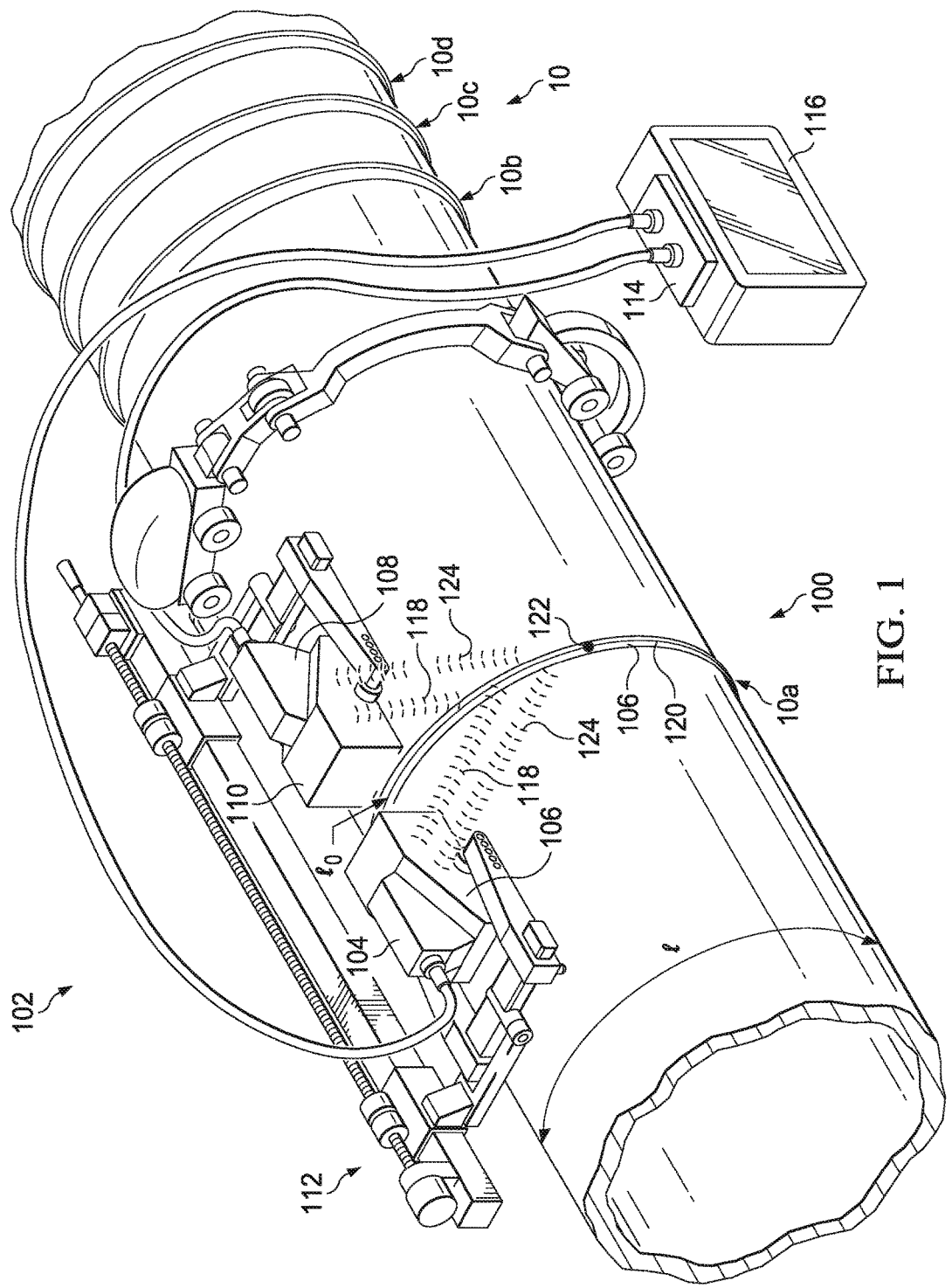
FIG. 1 depicts an enlarged perspective view of a phased array ultrasonic testing (PAUT) inspection of a welded joint within a welded object having a plurality of welded joints.

Embodiments of the present disclosure relate to the graphical representation and data presentation of weld inspection results. While the present disclosure is described herein with reference to illustrative embodiments for particular applications, it should be understood that embodiments are not limited thereto. Other embodiments are possible, and modifications can be made to the embodiments within the spirit and scope of the teachings herein and additional fields in which the embodiments would be of significant utility.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described. It would also be apparent to one skilled in the relevant art that the embodiments, as described herein, can be implemented in many different embodiments of software, hardware, firmware, and/or the entities illustrated in the figures. Any actual software code with the specialized control of hardware to implement embodiments is not limiting of the detailed description. Thus, the operational behavior of embodiments will be described with the understanding that modifications and variations of the embodiments are possible, given the level of detail presented herein.

As noted above, embodiments of the present disclosure relate to the graphical representation and data presentation of weld inspection results. The term "weld" is used herein to describe the deposit of material on an object, or the merging of at least two discrete objects by, for example, fusion, brazing, soldering, or the like. Unless otherwise noted for a specific embodiment, the welded object may be of any weldable material, including but not limited to metal or thermoplastics. In one or more embodiments, a system comprising an engine and external memory is used to generate a graphical representation of each welded joint for a plurality of welded joints which have been inspected using propagated energy type NDT, such as phased array ultrasonic testing (PAUT). The system also functions to extract, compile and present data related to the NDT inspection of the welded joints and the welded object. The engine may comprise an export module for extracting and processing data from the external memory. Additionally, the engine may comprise a transformation module for generating graphical representations of each welded joints using data obtained during the NDT inspection. Further, the engine may contain a merger module, which may compile the extracted data from the export module and the graphical representations from the transformation module into a user defined evaluation report format for each welded joint. The merger module may also combine each evaluation report into a comprehensive master report for presentation. The system may also include a graphical user interface (GUI) operable to allow a user to interface with the components of the system. For the purposes of discussion, propagated energy type NDT will be discussed herein in terms of phased array ultrasonic testing and the propagation of acoustic signals, but it should be understood that the system and methods described herein shall include any propagated energy type NDT unless otherwise limited. For example, X-ray signals may be utilized.

Illustrative embodiments and related methodologies of the present disclosure are described below in reference to FIGS. 1-6 as they might be employed, for example, in a computer system for the graphical representation and data presentation of weld inspection results. Other features and advantages of the disclosed embodiments will be or will become apparent to one of ordinary skill in the art upon examination of the following figures and detailed description. It is intended that all such additional features and advantages be included within the scope of the disclosed embodiments. Further, the illustrated figures are only exemplary and are not intended to assert or imply any limitation with regard to the environment, architecture, design, or process in which different embodiments may be implemented.

Referring to FIG. 1, an enlarged perspective view of a PAUT inspection tool 102 deployed on a welded object 100 having a plurality of welds 10 in the form of welded joints 10a, 10b, 10c and 10d is illustrated. Although the disclosure will present the method and system of the invention in terms of a welded joint, it will be appreciated that the method and system may be used for any weld. Likewise, although the welded object 100 is depicted as a pipe in FIG. 1, the welded object 100 may be any object, including, but not limited to, a rail, plate, vessel or tank. Further, the welded object 100 may be constructed of any material, including, but not limited to, high density polyethylene or any metal conducive to inspection by PAUT. The PAUT inspection of the welded joints 10 is performed using a PAUT inspection tool 102, which may be positioned adjacent a welded joint 10 of interest during the inspection. Alternatively, multiple PAUT inspection tools 102 may be deployed to inspect multiple welded joints simultaneously. Although the disclosure is not limited to a particular type of PAUT inspection tool, in certain embodiments, the PAUT inspection tool 102 may be comprised of a first transducer 104, a first wedge 106, a second transducer 108, a second wedge 110, a carriage 112, a pulser-receiver 114 and a phased array testing instrument (PATI) 116, as illustrated in FIG. 1.

During PAUT inspection of a welded joint 10a, for example, the PAUT inspection tool 102 may be moved along the periphery or scan length ("l") of the welded joint 10a, while the first and second transducers 104, 108 propagate acoustical signals 118 at spaced about locations along the periphery towards the welded plane 120 of the welded joint 10a. Typically, the PAUT inspection tool 102 will be positioned at an initial reference point $l_0$ and subsequently moved along scan length l for a desired distance. It will be appreciated that initial reference point $l_0$ is often top dead center of a pipe 100 under inspection. Upon encountering a discontinuity or flaw(s) 122 within the welded joint 10a, the acoustical signals 118 are reflected back (as reflected signals 124) towards the first and second transducers 104, 108. Reflected signals 124 may then be converted into electronic-amplitude signals by first and second transducers 104, 108 and transmitted to the pulser-receiver 114 of PATI 116. In one or more embodiments, this process may be performed multiple times. In some embodiments, the PAUT inspection tool 102 may be used to show a minimum of three reflected signals 124 for a welded joint 10 associated with the welded object 100. The reflected signal(s) are displayed in the form of traditional signal images, such as the A-scan, B-scan, S-scan or tomographic images discussed below in more detail with respect to FIG. 2.

Figure 2:
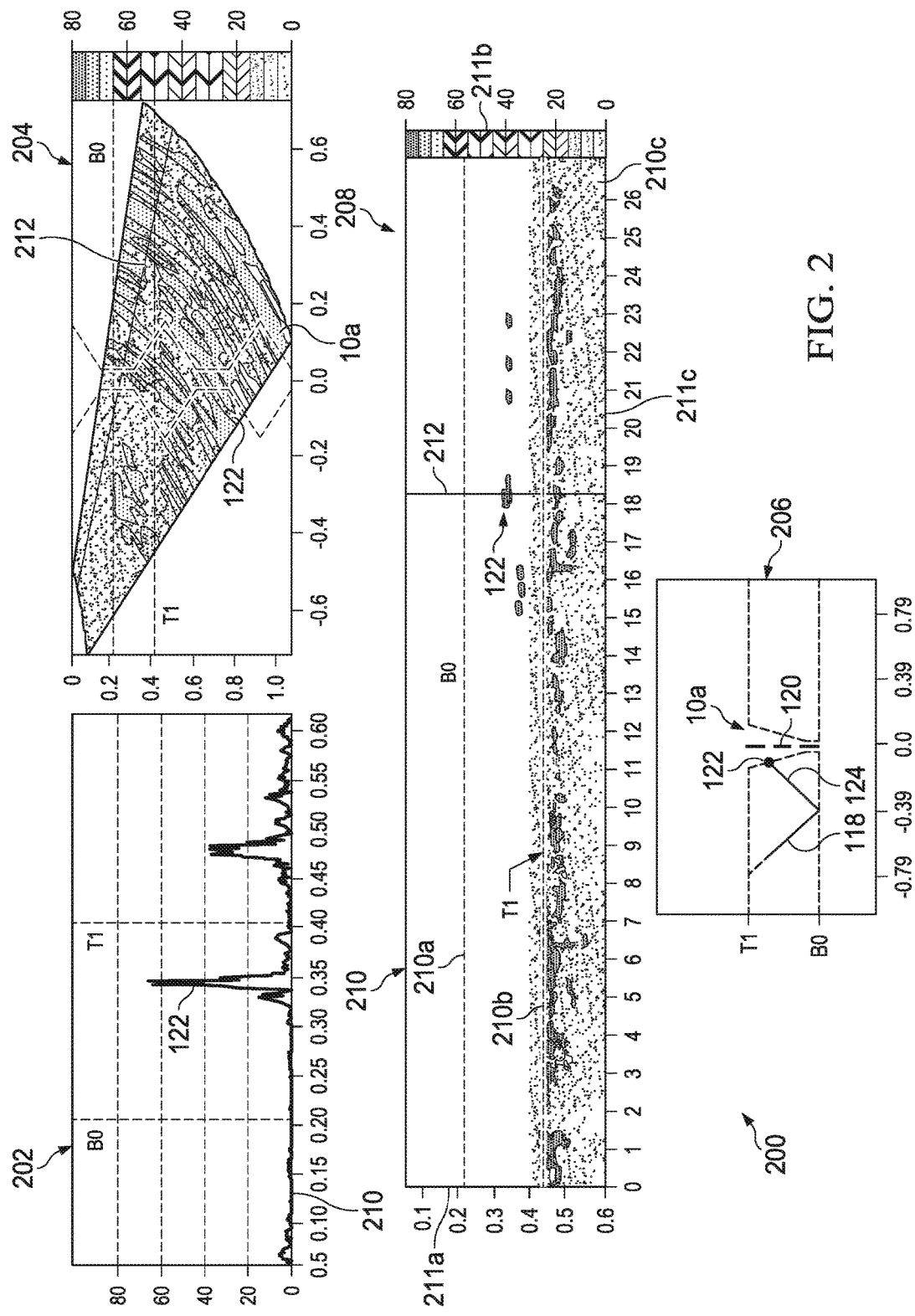
FIG. 2 depicts a display of plurality of ultrasound images generated from the PAUT inspection of a welded joint.

FIG. 2 illustrates a plurality of ultrasound images 200, displayed in various forms, generated by the PATI 116 during the PAUT inspection of the welded joint 10a associated with the welded object 100 of FIG. 1, as described above. In some embodiments, the ultrasound images 200 generated by the PATI 116 may include one or more of a waveform image such as an A-scan image 202; a S-scan image 204; a tomographic image 206; and a B-scan image 208, where a reflected signal or reflection 210 is illustrated. In each image, the top surface "T1" and the bottom surface "B0" of the welded joint 10a are denoted by either a horizontal or vertical line. The A-scan image 202 represents the waveform as the electronic-amplitude signal with respect to time. In FIG. 2, the A-scan image 202 illustrates the presence of a flaw 122, which is denoted by the peak between the top surface T1 and the bottom surface B0 of the welded joint 10a. The second peak does not indicate the presence of a flaw, but representation of extraneous sound from the inspection process. The S-scan image 204 represents a two dimensional cross-sectional view of the electronic-amplitude signals from transducers 104, 108 after being corrected for delay and refracted angle. In FIG. 2, the S-scan image 204 depicts the waveform image results of propagating acoustic signals 118 from the top surface T1 of the welded joint 10a at a scan range between 45 and 70 degrees. The tomographic image 206 represents a two dimensional cross-sectional grid visualization of the welded joint 10. In FIG. 2, the tomographic image 206 is a Ray-Tracing image which illustrates the acoustic signal 118 and the reflected signal 124 being propagated through the welded joint 10a area. The B-scan image 208 depicts a two dimensional representation of the electronic-amplitude signals as plotted relative to depth or distance over the scan length ("l") or perimeter of the welded joint 10a.

It will be appreciated that an aberration in the weld 10 of a welded joint 10a may result in change in the waveform images and that if the aberration is significant enough, it may be deemed a flaw 122 or a flaw 122 indication. For example, as discussed above, in the waveform image illustrated by the A-scan image 202, the first signal peak resulting from an aberration in the weld 10 is an indication of a flaw 122 as shown. Likewise, reflection flaw indications 122 are identified in B-scan image 208 and tomographic image 206 as shown.

As will be explained below, in one or more embodiments, a PAUT inspection tool 102 may make multiple passes along a welded joint 10. For example, a PAUT inspection tool 102 may be passed around the circumference of a pipe along a welded joint 10 two or more times, wherein each pass results in a set of reflection data such that an overall reflection 210 for any given location along the welded joint 10 may be comprised of two or more reflections 210a, 210b, 210c, etc. Thus, the PAUT inspection tool 102 may be used to scan a segment of a welded joint 10a multiple times with each pass of the PAUT inspection tool 102 represented on the B-scan image 208 as a separate reflection 210a, 210b, and 210c. The PAUT inspection tool 102 may be used to scan any desired segment of the weld 10 of a welded joint 10a of a welded object 100. In one or more embodiments, the welded object 100 is a pipe and the scan length l may correspond to an area or surface along the periphery of the welded object 100. In such embodiments, as previously discussed, the movement of the PAUT inspection tool 102 about the circumference of a pipe along the welded joint 10a results in the creation of at least three reflected signals 124. Accordingly, the PATI 116 produces a B-scan image 208 with at least three reflections 210 shown on the display: a first reflection 210a, a second reflection 210b and a third reflection 210c presented in a vertical array orientation of the welded joint 10a. The first reflection 210a represents the travel of the acoustic signal 118 from the top surface T1 of the welded joint 10a to the bottom surface B0 of the welded joint. The second reflection 210b represents the travel of the reflected signal 124 from the bottom surface B0 of the welded joint 10a to the top surface T1 of the welded joint 10a. The third reflection 210c represents the travel of the reflected signal 124 from the top surface T1 of the welded joint 10a to the bottom surface B0 of the welded joint 10a. The left vertical axis 211a of the reflection 210 represents the depth of the welded joint 10 relative to the surface (such as the surface of pipe of FIG. 1) along which the PAUT inspection tool 102 is moved. The right vertical axis 211b of the reflection 210 represents the strength of the electronic-amplitude signal converted by the transducers 104, 108 and received by the PATI 116. The horizontal axis 211c of the reflection 210 represents the perimeter or scan length of welded joint 10a. During the PAUT inspection, the reflections 210 may include areas representing flaws 122 within the welded joint under inspection. The presence of a flaw 122 in the reflection may be emphasized with a flaw indication line 212. In some embodiments, PAUT inspection tool 102 may include predetermined flaw identification criteria that can be utilized by PAUT inspection tool 102 to identify aberrations in the waveform images that are significant enough to be deemed a flaw 122. In other embodiments, a user may identify such flaws 122 for PAUT inspection tool 102.

It will be appreciated with respect to the horizontal axis 211c, "0" simply represents the point around the perimeter at which the scan begins and in this way, corresponds to reference point $l_0$ on the welded object 100 under inspection. In one or more embodiments, this reference point may be utilized as the beginning of each scan of the particular welded joint 10a under inspection, or any subsequent scans should be conducted in measured relation to this reference point.

In addition to the plurality of ultrasound images 200 generated and displayed by PATI 116, PATI 116 may be configured to extract and/or compile PAUT data from the PAUT inspection. In certain embodiments, the PAUT data may comprise, but is not limited to, spatial and magnitude information related to an identified flaw 122 (flaw data), positional information related to the inspection, such as the reference point $l_0$ discussed above and incremental spacing relative to the reference point, information related to the equipment (e.g. transducers 104, 108 or wedges 106, 110) used during the PAUT inspection (PAUT inspection equipment data), information related to the calibration of equipment used during the PAUT inspection (PAUT inspection calibration data) and information related to the welding design parameters of the plurality of welded joints 10a, 10b, 10c, 10d, etc. and the welded object 100.

Figure 3A:
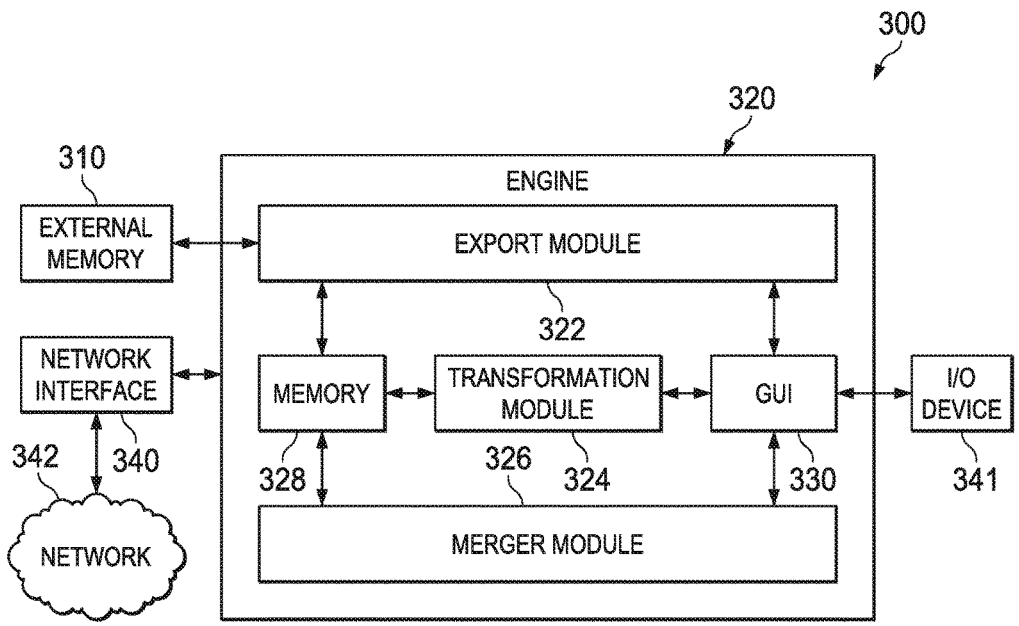
FIG. 3A is a block diagram of an exemplary system for the graphical representation and data presentation of a plurality of welded joints within a welded object.

FIG. 3A is a block diagram of an exemplary system 300 for the graphical representation and data presentation of weld inspection results. As shown in FIG. 3A, system 300 may include an external memory 310 and an engine 320. In some embodiments, the engine 320 includes an export module 322, a transformation module 324, a merger module 326, a memory 328 and a GUI 330. Further, in certain embodiments the engine 320, export module 322, transformation module 324, merger module 326, memory 328 and GUI 330 may be communicatively coupled to one another via an internal bus (not shown) of system 300. In some embodiments the engine 320 may be operably and communicatively coupled to a network interface 340.

In an embodiment, system 300 can be implemented using any type of computing device having at least one processor and a processor-readable storage medium for storing data and instructions executable by the processor. Such a computing device may also include an input/output (I/O) device 341 for receiving input or commands or displaying information or graphics. The input/output device 341 may be, for example and without limitation, a mouse, a QWERTY or T9 keyboard, a touch-screen, a graphics tablet, or a microphone. The I/O device 341 also may be, for example, a display or printer coupled to or integrated with the computing device for displaying a graphical representation and presentation of inspection results in accordance with this disclosure. Examples of such a computing device include, but are not limited to, a mobile phone, a personal digital assistant (PDA), a tablet computer, a laptop computer, a desktop computer, a workstation, a cluster of computers, a set-top box, a PATI 116, or similar type of computing device.

Although only an external memory 310 and an engine 320 including an export module 322, a transformation module 324, a merger module 326, a memory 328 and a GUI 330 along with a network interface 340 are shown in FIG. 3A, it should be appreciated that system 300 may include additional components, modules, and/or sub-components as desired for a particular implementation. It should also be appreciated that each of the external memory 310 and an engine 320 including export module 322, transformation module 324, merger module 326, memory 328, and GUI 330 may be implemented in software, firmware, hardware, or any combination thereof. Furthermore, it should be appreciated that embodiments of the external memory 310 and an engine 320 including export module 322, transformation module 324, merger module 326, memory 328, and GUI 330 or portions thereof, can be implemented to run on any type of processing device including, but not limited to, a computer, workstation, embedded system, networked device, mobile device, or other type of processor or computer system capable of carrying out the functionality described herein.

As will be described in further detail below, external memory 310 may be used to store information accessible by the engine 320 and memory 328 may be used to store information accessible by each of the export module 322, transformation module 324, merger module 326 and GUI 330 for implementing the functionality of the present disclosure. External memory 310 and memory 328 may be any type of recording medium coupled to an integrated circuit that controls access to the recording medium. The recording medium can be, for example and without limitation, a semiconductor memory, a hard disk, or similar type of memory or storage device. In some implementations, external memory 310 and memory 328 may be a remote data store, e.g., a cloud-based storage location, communicatively coupled to system 300 over a network 342 via network interface 340. Network 342 can be any type of network or combination of networks used to communicate information between different computing devices. Network 342 can include, but is not limited to, a wired (e.g., Ethernet) or a wireless (e.g., Wi-Fi or mobile telecommunications) network. In addition, network 342 can include, but is not limited to, a local area network, medium area network, and/or wide area network such as the Internet.

The plurality of ultrasound images 200 and PAUT data from the PAUT inspection may be transferred from the PATI 116 to the external memory 310. This transferred information may be grouped within the external memory 310 by parameters associated with the welded joint 10a including, but not limited to, weld length, weld position or weld type. Via the GUI 330, the export module 322 of the engine 320 may be implemented to export the plurality of ultrasound images 200 and PAUT data from the PAUT inspection from the external memory 310 to the memory 328 of the engine 320. In some embodiments, the export module 322 operates to determine whether the PAUT inspection data has been improperly grouped within the external memory 310. For instance, if the PAUT data and plurality of ultrasound images 200 from the PAUT inspection is grouped by a specified scan length ("l") of the plurality of welded joints 10a, 10b, 10c, 10d, etc., the export module 322 may be operable to determine if all of the information within the external memory 310 from the PAUT inspection meets the selected grouping criteria. If not, the export module 322 may trigger an alert through the GUI 330 when a potential inconsistency is identified. The export module 322 may also expand the reporting to combine the reporting of each grouping.

The export module 322 may also be configured to search the plurality of ultrasound images 200 within the memory 328 of the engine 320 to determine whether a flaw 122 indication was determined to be present in the data and scans associated with the plurality of welded joints 10a, 10b, 10c, 10d, etc., of the welded object 100. The export module 322 may communicate the results of this search to the GUI 330 to display of the plurality of welded joints 10a, 10b, 10c, 10d, etc., in which at least one flaw indication 122 was identified. In some embodiments, the export module may identify acceptable welds (i.e. welds in which no flaw indications were deemed to be present) and communicate the results of this determination to the GUI 330 to display the plurality of welded joints 10a, 10b, 10c, 10d, etc., in which no flaw 122 was identified.

Figure 3B:
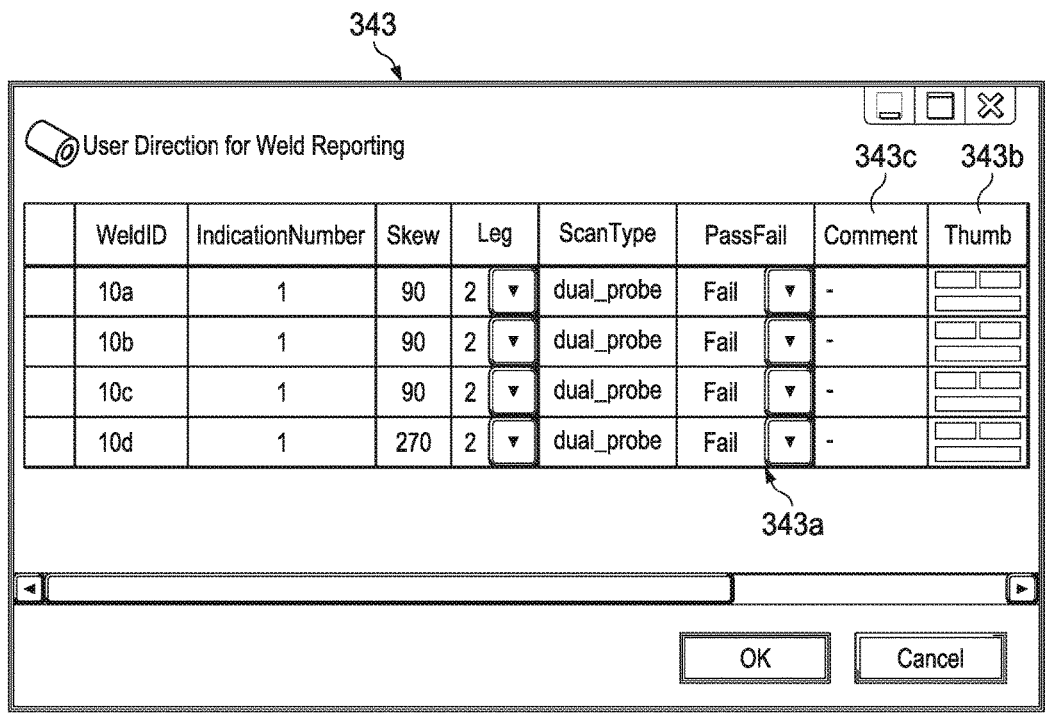
FIG. 3B depicts an exemplary view of a listing of welded joints with flaw indications within the welded object presented within an interactive window of a graphical user interface (GUI), according to one or more illustrative embodiments.

FIG. 3B illustrates an exemplary view of an interactive flaw indication screen 343 listing the plurality of welded joints 10a, 10b, 10c, 10d, etc., identified by the PAUT inspection as containing flaws 122. In some embodiments, the interactive flaw indication screen 343 may contain an information field 343a which reflects whether the welded joint 10 passed or failed the PAUT inspection. In this regard, the system 300 may make a determination based on predetermined parameters. For example, in some embodiments, the presence of even a single flaw 122 may result in rejection of the weld, while in other embodiments, a multiple flaws 122 may be need to be present before a weld is rejected. Likewise, the characteristics of the flaw 122 may have a bearing on whether a weld is accepted or rejected, which characteristics may include physical size of the flaw 122, flaw 122 depth or proximity to other flaws 122, any or all of which may be pre-programed into system 300 or otherwise supplied to system 300. Further, in some embodiments, the interactive flaw indication screen 343 may contain an information field 343b which allows the presentation of a plurality of ultrasound images 200 related to the inspection of the selected welded joint 10 within the GUI 330 and a comment field 343c into which notes, comments or other information pertaining to the welded joint 10 may be added.

Additionally, the flaw indication screen 343 allows a user to select which reflections 210 from the B-scan image 208 best illustrate the flaw 122 identified during the PAUT inspection, and which reflections 210 will be used to generate a multi-dimensional image of the welded joint 10a. In some embodiments, the multi-dimensional image is a three dimensional ("3-D") image of the welded joint 10a. The information fields which appear in the interactive flaw indication screen 343 may be selectable by a user. For instance, in some embodiments, users may add an information field 343d indicating the type of scan used during the PAUT inspection and the skew of the flaw 122. At the point when at least one reflection 210 is chosen for a welded joint 10 containing a flaw 122 or the export module 322 fails to find any flaws amongst the plurality of ultrasound images 200, the transformation module 324 of the engine 320 may be implemented, either automatically in response to predetermined criteria or by a user via GUI 330.

Figure 3E:
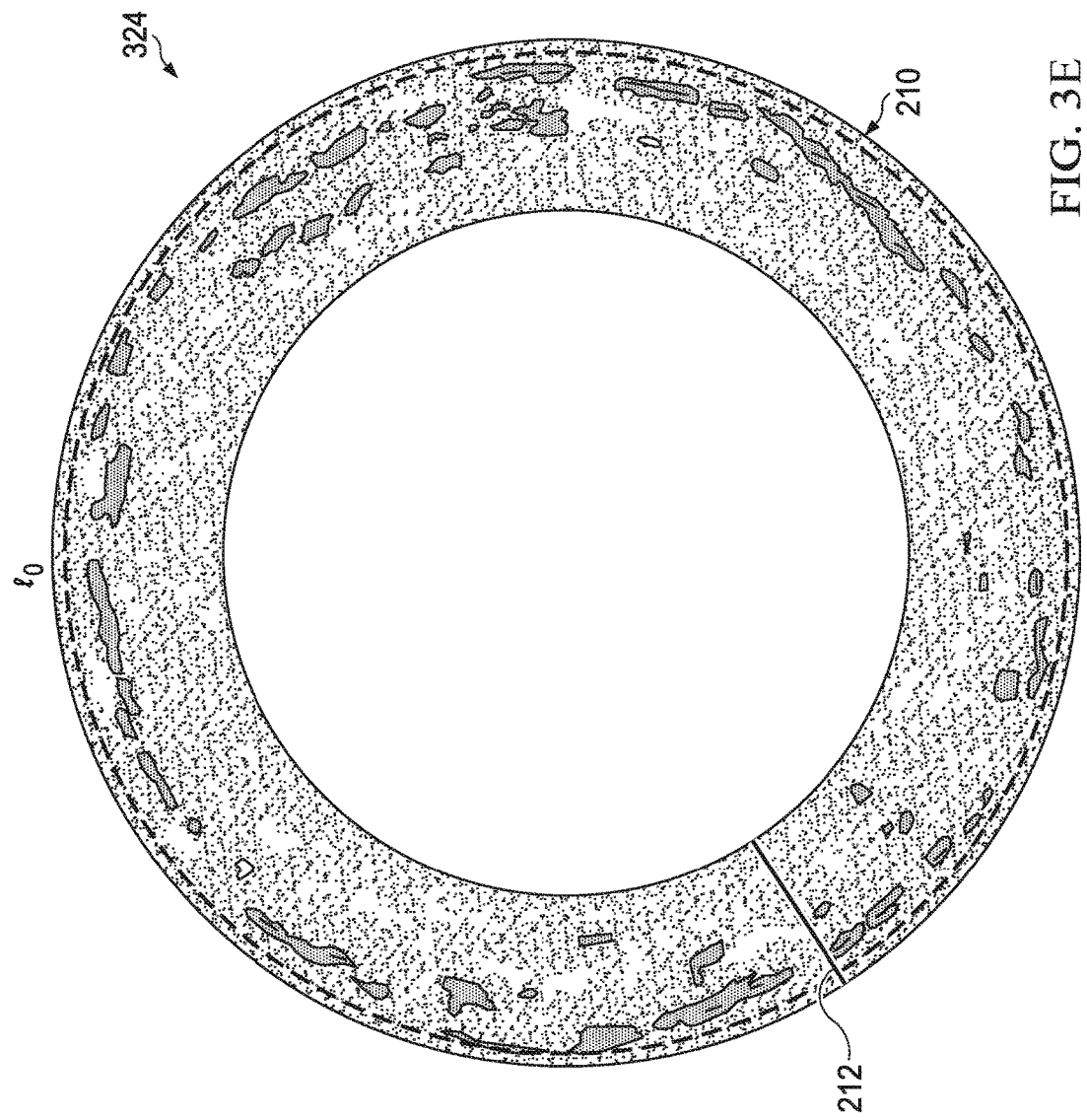
FIG. 3E depicts an enlarged view of the reflection of FIG. 3D transformed into the shape of a cross-sectional representative image of the welded joint.
Figure 3F:
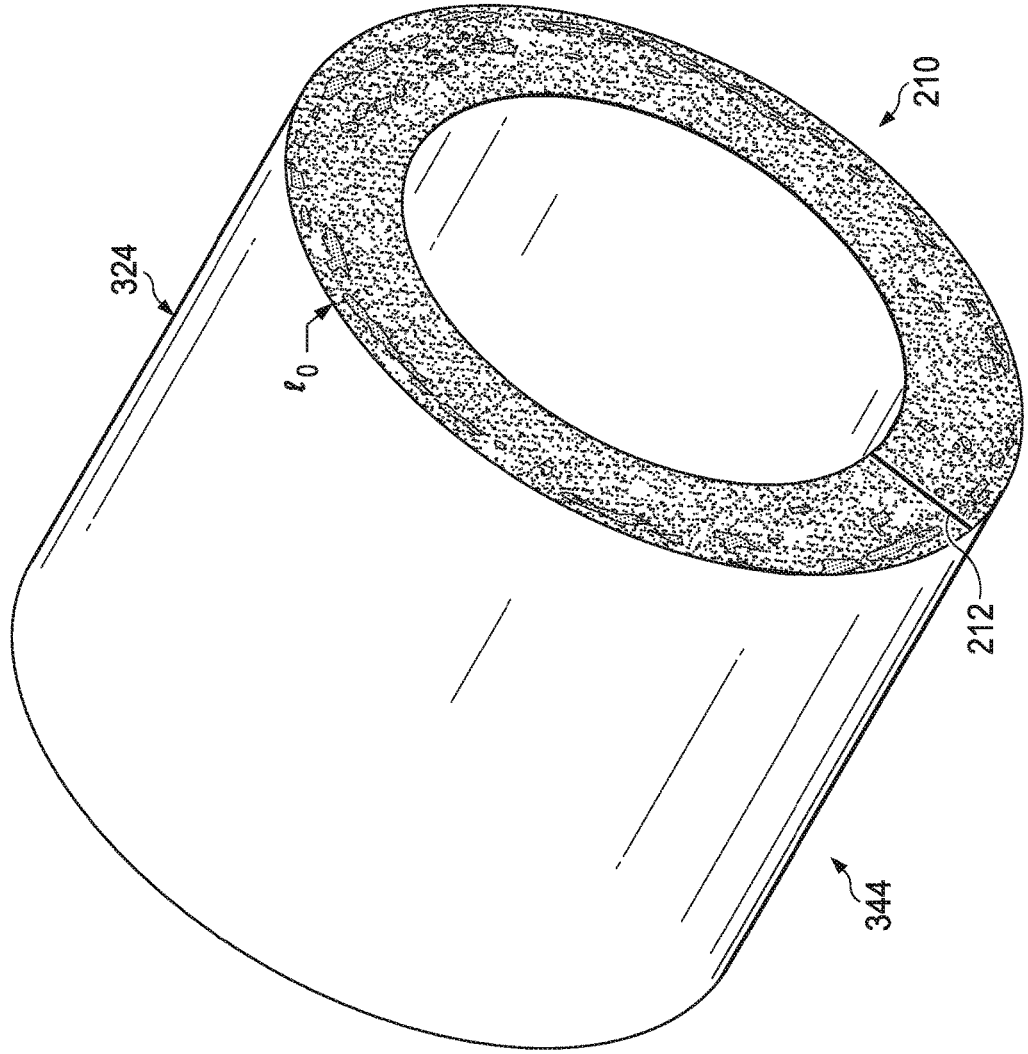
FIG. 3F depicts an enlarged perspective view of the transformed reflection of FIG. 3E superimposed on a three dimensional representative image of the welded joint, according to one or more illustrative embodiments.

FIGS. 3C, 3D, 3E and 3F illustrate the process used to by the transformation module 324 to create a multi-dimensional representation 344 of the PAUT inspected welded joint 10. While a two-dimensional ("2-D") representation is within the scope of this disclosure, in some embodiments, the representation is three-dimensional. In some embodiments, the transformation module 324 may comprise image manipulation libraries which contain 2-D and/or 3-D shapes and/or image data of the object 100 and the welded joint 10 under investigation. In one or more embodiments, a user may select a shape most closely resembling the shape of the object 100, and then supply dimensional information relative to the shape to be included with the PAUT data. For example, a user may select a pipe shape from the library and then supply an outer diameter, and inner diameter, a pipe length and optionally, relative location of the welded joint 10 under investigation. FIG. 3C represents an enlarged view of the B-scan image 208 taken from a plurality of ultrasound images 200 of the welded joint 10a. Once the reflections 210 to be used in creating the representation 344 of the welded joint 10a have been selected, the transformation module 324 may use the image manipulation library to extract the selected reflection 210 as shown in FIG. 3D from the memory 328. The transformation module 324 then manipulates the selected reflection 210 into the shape of a cross-sectional representative image of the welded joint 10a as shown in FIG. 3E. It will be appreciated at this point, a 2-D cross-section of the object 100 overlaid with the manipulated reflections 210 may be presented and utilized to graphically visualize the weld data on the object 100. A reference point $l_0$ on the object 100 is utilized to align the manipulated reflections 210 relative to the object 100, while flaw indication line 312 identifies a detected flaw relative to reference point $l_0$. For example, reference point $l_0$ may be the location on the surface of object 100 at which the first acoustical signal 118 is propagated into the weld 10. The reference point $l_0$ may also be used as a basis for incrementally moving the PAUT and propagating a subsequent acoustical signal 118. In other embodiments, an additional step may be taken to convert the 2-D representation to a 3-D representation. In this regard, the transformation module 324 obtains the 3-D image data of the object 100 and the welded joint 10a under investigation from the image manipulation libraries and superimposes and aligns the manipulated reflections 210 onto a 3-D image of the object 100 to create the 3-D representation 344 of the PAUT inspected welded joint 10a as depicted in FIG. 3E. This process may be repeated for each flaw 122 or selected flaws 122 identified within each weld 10.

This 2-D or 3-D representation process may be performed for one or more weld 10 within the welded object 100, regardless of whether the PAUT inspection indicates a flaw 122 is present within the welded joint 10a. For example, the transformation module 324 by default may select the first reflection 210a to be used in creating the 3-D representation 344 of the welded joint 10a when no flaw 122 has been identified in the PAUT inspection.

In any event, once the transformation module 324 has completed this 2-D or 3-D representation process for one or more welded joints 10 in the plurality of welded joints 10a, 10b, 10c, 10d, etc. within the welded object 100, the representations 344 of a PAUT inspected welded joint 10a are stored in memory 328 for use by the merger module 326.

Figure 3G:
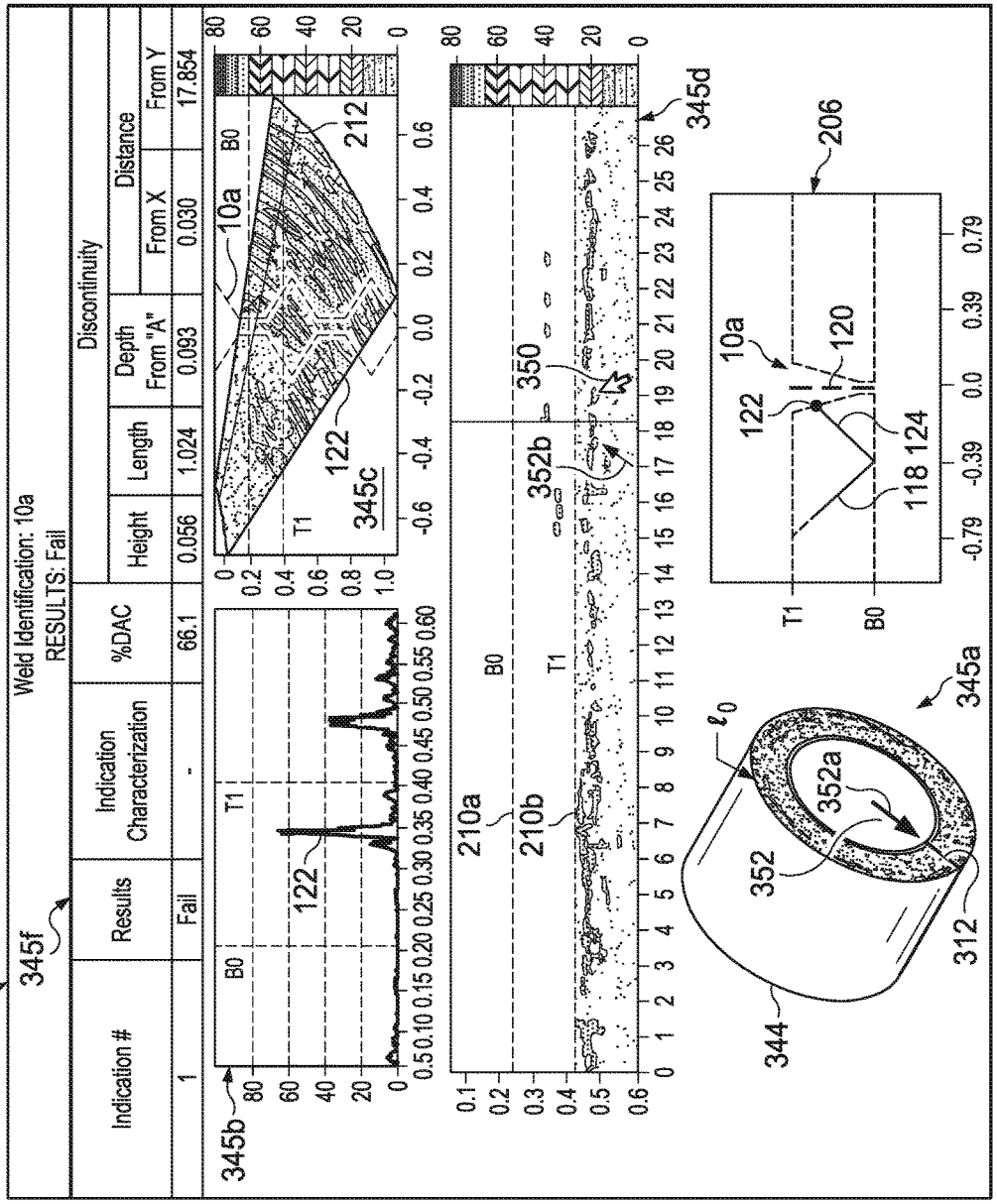
FIG. 3G depicts an illustration of an exemplary evaluation report generated for each welded joint, according to one or more illustrative embodiments.

After a representation 344 of a PAUT inspected weld 10 within the welded object 100 has been created, the merger module 326 may be used by the engine 320 to create an evaluation report 345 for a welded joint 10, whether a flaw 122 has been detected or not, within the plurality of welded joints 10a, 10b, 10c, 10d, etc., of the welded object 100 as illustrated in FIG. 3G. The evaluation report 345 includes a first field 345a to present the generated 2-D or 3-D representation 344 of the PAUT inspected welded joint 10. The evaluation report 345 may include other fields to display information associated with the particular representation 344 shown in field 345a. It will be appreciated that the report 345 is not limited to display of particular fields or data, but that the fields may be predetermined or selectable, as desired. For example, in FIG. 3G, in addition to field 345a showing a 3-D representation 344 associated with a particular weld 10, a second field 345b shows the A-scan image 202, a third field 345c shows an S-scan image 204, a fourth field 345d shows a B-scan image 208, a fifth field 345e shows a tomographic image 206 and a sixth field 345f shows numeric data related to the weld 10 and the flaw 122.

In one or more embodiments, the report 345 may be interactive. In this regard, a cursor 350 may be utilized to point to a particular location within a desired field. In response, a visual indicator 352 may be presented in one or more of the other fields to indicate a graphical relationship between where the cursor 350 is pointing and the information presented in the other fields. For example, in FIG. 3G, a cursor 350 may be utilized to point to a particular position on the S-scan image 204 in field 345c. In response, a first visual indicator 352a may point to the corresponding location on the 2-D or 3-D representation 344 in field 345a. Likewise, in one or more embodiments, a second visual indicator 352b may point to the corresponding location on the B-scan image 208 in field 345d. Similarly, moving the cursor 350 to point to a particular location on the 2-D or 3-D representation 344 in field 345a may result in one or visual indicators 352 in fields 345b-345f. As used herein, visual indicator is not limited to any particular visual device, and may include a graphical device (such as an arrow, crosshairs, a circle or other graphical objects) highlights, color change or text, among others.

In any event, the merger module 326 may contain (i) a database template to designate the display locations of the information fields representing the 2-D or 3-D representation 344 the PAUT inspected welded joint 10, (ii) selected inspection data from the PAUT inspection and (iii) the exported plurality of ultrasound images 200 to be presented within the evaluation report 345. Although FIG. 3G illustrates information fields representing a weld identification number, the number of flaws 122 identified in the welded joint 10, and spatial and magnitude information related to the identified flaws 122, these information fields may be modified and may be predetermined or otherwise selectable by the (I/O) device 341 from the range of PAUT inspection data stored within the memory 328. In this regard, the merger module 326 may be configured to store templates comprising preselected information fields to be presented in the evaluation report 345.

Once implemented, the merger module 326 functions to extract selected PAUT inspection data and ultrasound images 200 stored in memory 328 from the export module 322 and the 2-D or 3-D representation 344 of the PAUT inspected welded joint 10 from the transformation module 324 for the welded joint 10. The merger module 326 then presents this data in the designated display locations of the fields within the database template and displays this on an output device, which may be saved as an electronic file. A portable document format (PDF) file for the evaluation report 345 representing the welded joint 10 may also be generated. In some embodiments, an editable word processing document for the evaluation report 345 representing the welded joint 10a may also be generated. In the event the PAUT inspection indicates the welded joint 10 contains more than one flaw, the merger module 326 may create an evaluation report 345 file for each flaw 122 identified.

After an evaluation report 345 representing one or more welded joints 10a within the welded object 100 has been created, the merger module 326 may combine the files of each evaluation report 345 into a master report. In some embodiments, the merger module 326 may extract and include a summary of the PAUT inspection equipment data, PAUT calibration data, and the welding design parameters of the plurality of welded joints 10a, 10b, 10c, 10d, etc. within the welded object 100 for inclusion in the master report.

When a welded joint 10a is determined to contain a flaw 122, various corrective measures may be implemented to remove and repair it. For instance, the spatial parameters of the flaw 122 within the welded joint 10a are documented and the welded joint 10 containing the flaw 122 may be physically marked. The surface of the welded joint 10a may then be ground down to the documented depth of the flaw 122 for removal. Alternatively, an arc-gouging approach may be implemented to remove the flaw 122. In this method, an electric arc is generated using a carbon electrode to make the welded joint 10*a* become molten and to produce high velocity air jet streams for removal of the molten material. In either approach, once the flaw 122 is removed from the welded joint 10, the previously welded joint 10*a* is re-welded and re-inspected.

Figure 4:
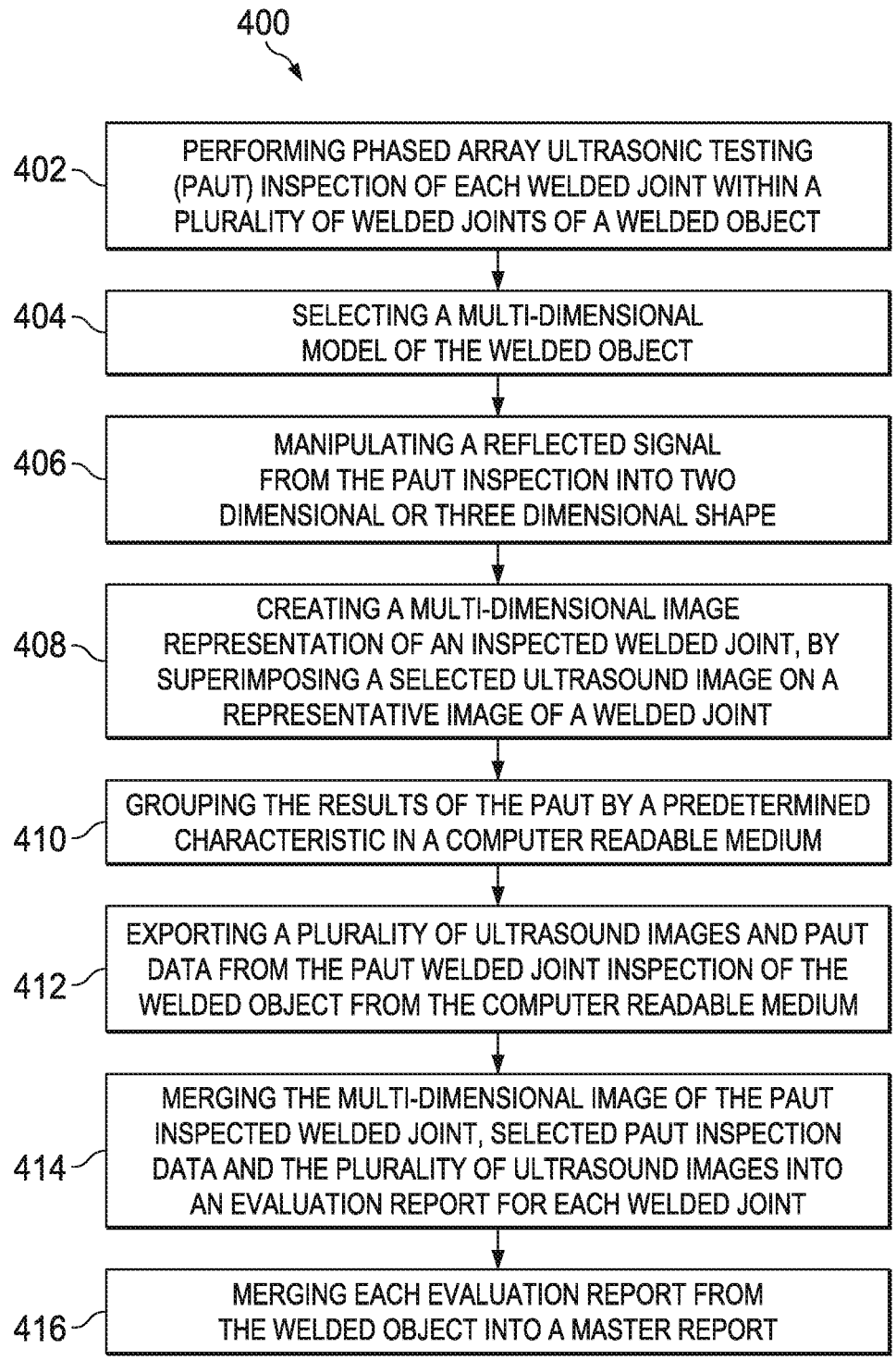
FIG. 4 is a flowchart illustrating an exemplary method for the graphical representation and data presentation of a plurality of welded joints within a welded object.

FIG. 4 is a flow chart of an exemplary method 400 for the graphical representation and data presentation of weld inspection results. As shown in FIG. 4, method 400 includes steps 402, 404, 406, and 408, and may further include at least one of steps 410, 412, 414 and 416. For purposes of discussion, method 400 will be described using system 300 of FIG. 3A, as described above. However, method 400 is not intended to be limited thereto.

Method 400 begins in step 402, which includes performing a PAUT inspection of one or more welds 10 of a welded object 100. For example, the inspection may be of welded joints 10*a*, 10*b*, 10*c*, 10*d*, etc. A PAUT inspection tool 102 is used to propagate acoustic signals 118 into a welded object 100 adjacent a weld 10. To the extent the welded object 100 is a pipe and the weld 10 is a welded joint, the PAUT inspection tool 102 may be moved along a portion of or the entire periphery of the pipe adjacent the weld 10. In one or more embodiments, for each weld 10, this process may be repeated multiple times. In any event, at least three reflected signals 124 are generated upon encountering a welded plane 120 or a flaw 122 along the welded joint 10. The reflected signals 124 may be converted to electronic-amplitude signals and are transmitted to a PATI 116 of the PAUT inspection tool 102. The PATI 116 may display the converted electronic amplitude signals in the form of a plurality of ultrasound images 200, which may include a B-scan image 208. B-scan image 208 may comprise an array of reflections 210 and may represent each complete pass of the PAUT inspection tool 102 along a welded joint 10. It will be appreciated that the disclosure is not limited to particular equipment in performing the PAUT inspection so long as a reflected signal 124 is generated for one or more flaws 122 within a weld 10.

The PATI 116 may also be configured to extract and compile PAUT data from the PAUT inspection including, but not limited to, flaw 122 data, inspector comments, PAUT inspection equipment data PAUT calibration data, and welding design parameters of the plurality of weld 10 (such as welded joints 10*a*, 10*b*, 10*c*, 10*d*, etc.) and the welded object 100.

In step 404, a multi-dimensional model of the welded object 100 is selected or otherwise generated. In this regard, a library of models may be maintained and the model most closely resembling the welded object 100 may be selected. For example, a model library may contain a two-dimensional or three-dimensional representation of a pipe, a plate, a beam or some other object. A model may be selected from the library that most closely resembles the welded object 100. In one or more embodiments, the user may be queried about the dimensioning and/or parameters of the welded object 100 under investigation this data may be associated with the selected model. For example, a pipe may be selected from the model library to represent a welded object 100 being inspected. The user may be queried about the inner diameter, the outer diameter and length of the welded object 100 and the dimensioning data may be utilized to generate a proportional image of the welded object 100 accordingly.

Alternatively in step 404, the user may simply be queried about the dimensioning and/or parameters of the welded object 100 under investigation this data may be used to generate an image of the welded object 100 under investigation. For example, a user may input an inner diameter, an outer diameter and a length for a welded object 100. Using this data, an image of the welded object 100 may be generated.

Likewise, a user may be queried about the welds. For example, the number of welds and/or the location of the welds may be provided so that each weld may be separately accounted for as necessary.

In any event, the generated image may be a two-dimensional object or a three-dimensional object, as desired.

In step 406, the reflected signal 124 data is manipulated to conform the data to a two-dimensional or three-dimensional shape. In one or more embodiments, the reflected signal data may be in the form of an ultrasound image. Thus, for example, a point on the ultrasound image may be associated with a particular two or three dimensional point on the shape. In other words, each point on the ultra-sound or each point along an A-scan image 202, or an S-scan image 204 may be assigned or associated with a two or three dimensional coordinate. This coordinate data may be used to link the reflected signal data to the generated image of the welded object 100.

In step 408, the manipulated reflected signal data is superimposed on the generated image of the welded object 100 and the superimposed image is graphically presented as a multi-dimensional representation 344 of the PAUT inspected weld 10. In this regard, the manipulated reflected signal data must be aligned with the generated image of the welded object 100 to yield the multi-dimensional representation 344.

This foregoing process may be repeated for each flaw 122 identified within each weld 10 and is similarly performed for each welded joint 10 within the welded object 100.

In one or more embodiments, prior to manipulating reflected signal data, a specific reflection 210 is selected from multiple reflections associated with a particular flaw 122. As mentioned above, in some embodiments, multiple passes of a weld 10 may be made with the PAUT inspection tool 102, and thus, multiple sets of reflection data may exist, making it necessary to select the particular data set to be manipulated in step 406. In this regard, the flaw indication screen 343 may be used to choose one reflection 210 for each welded joint 10 determined to contain a flaw 122. If a reflection 210 is chosen, the transformation module 324 may use an image manipulation library to extract the selected reflection 210 from the memory 328. The transformation module 324 then manipulates the selected reflection 210 into the shape of a cross-sectional representative image of the weld 10 and obtains from the image manipulation library, or otherwise generates, a multidimensional digital image representative of the welded joint 10.

The transformation module 324 then superimposes and aligns the manipulated image onto the multidimensional image to create the representation 344 of the PAUT inspected welded joint 10.

In one or more embodiments, in an optional additional step 410, a plurality of ultrasound images may be generated for a weld 10 or a welded object 100, and the plurality of ultrasound images 200 and the PAUT data from the PAUT inspection are transferred from the PATI 116 to a memory, and may be grouped within the memory by parameters associated with weld 10, such as weld number, weld length, weld position or weld type. In this regard, the memory may be external memory 310.

In one or more embodiments, in an additional optional step 412, an export module 322 of an engine 320 comprising memory 328 and a GUI 330 may be used to export the plurality of ultrasound images 200 and PAUT data from the PAUT inspection from the external memory 310 to the memory 328 of the engine 320. In some embodiments, the export module 322 is configured to determine whether the PAUT inspection data has been improperly grouped within the external memory 310. Further, export module 322 may be configured to search the plurality of ultrasound images 200 within the memory 328 of the engine 320 to determine whether a flaw 122 was identified by an inspector in each of the plurality of welded joints 10a, 10b, 10c, 10d, etc., of the welded object 100 and to display a listing of the welded joints 10 containing flaws 122 on an interactive flaw indication screen 343 within the GUI 330. The flaw indication screen 343 is operable to facilitate the selection of which reflections 210 from the B-scan image 208 best illustrates the flaw 122 identified during the PAUT inspection and which reflections 210 will be used to generate a 3-D image of the welded joint 10.

In one or more embodiments, in an additional optional step 414, the engine further comprises a merger module that creates an evaluation report 345 for each weld 10 of the welded object 100. The merger module 326 contains a database template to designate the display locations of the fields representing the multidimensional representation 344 the welded object 100, selected inspection data from the PAUT inspection and the exported plurality of ultrasound images 200 within the evaluation report 345. Once implemented, the merger module 326 may function to extract the 341 selected PAUT inspection data and ultrasound images 200 stored in memory 328 from the export module 322 and the representation 344 of each PAUT inspected weld 10 from the transformation module 324 for each weld 10. The merger module 326 then imports this data to the designated display locations of the fields within the database template and creates digital document which may be presented on an output device or otherwise saved for an evaluation report 345 representing each welded joint 10. In the event the PAUT inspection indicates the weld 10 contains more than one flaw, the merger module 326 will create an evaluation report 345 for each flaw 122 identified.

Finally in one or more embodiments, in an additional optional step 416, the merger module 326 operates to merge each evaluation report 345 file into a master report PDF or word processing editable file for presentation. The merger module 326 is operable to extract and include a summary of the PAUT inspection equipment data, PAUT calibration data, and the welding design parameters of the plurality of welded joints 10a, 10b, 10c, 10d, etc. within the welded object 100 for inclusion in the master report.

Figure 5:
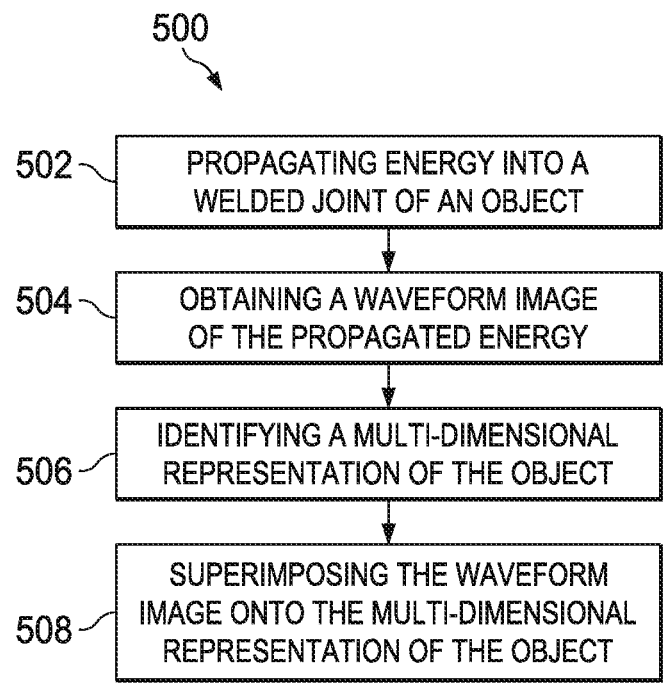
FIG. 5 is a flowchart illustrating an alternate method for the graphical representation and data presentation of a plurality of welded joints within a welded object.

FIG. 5 is a flow chart of an alternative method 500 for the graphical representation and data presentation of weld inspection results. For purposes of this discussion, method 500 is described using system 300 of FIG. 3A; however, method 500 in not intended to be limited thereto. Method 500 begins in step 502 by propagating energy into a welded joint 10a of a welded object 100. In an embodiment, a PAUT inspection tool 102 may be used to propagate either acoustic energy into a welded object 100 adjacent a welded joint 10a. To the extent the welded object 100 is a pipe, the PAUT inspection tool 102 may begin at a reference point $l_0$ on the pipe and may be moved along the entire circumference of the pipe adjacent the welded joint 10. Alternatively, the PAUT inspection tool 102 may be only moved along the circumference of the pipe that has been welded.

As the PAUT inspection tool 102 is moved along the circumference of the pipe, in step 504 a waveform image of the propagated energy is obtained by the PAUT inspection tool 102. In certain embodiments the acoustic energy returns to the PAUT inspection tool 102 in the form of reflected signals 124 which may be converted to electronic-amplitude signals and displayed as a variety of waveform images such as an A-scan image 202, a S-scan image 204, a tomographic image 206 or a B-scan image 208.

In step 506 a multidimensional representation of the object welded 100 is identified. In this regard, a library of models may be maintained and the model most closely resembling the welded object 100 may be selected. For example, a model library may contain a two-dimensional or three-dimensional representation of a pipe, a plate, a beam or some other object. A model may be selected from the library that most closely resembles the welded object 100. In one or more embodiments, the user may be queried about the dimensioning and/or parameters of the welded object 100 under investigation this data may be associated with the selected model. For example, a pipe may be selected from the model library to represent a welded object 100 being inspected. The user may be queried about the inner diameter, the outer diameter and length of the welded object 100 and the dimensioning data may be utilized to generate a proportional image of the welded object 100 accordingly.

Alternatively in step 506, the user may simply be queried about the dimensioning and/or parameters of the welded object 100 under investigation this data may be used to generate an image of the welded object 100 under investigation. For example, a user may input an inner diameter, an outer diameter and a length for a welded object 100. Using this data, an image of the welded object 100 may be generated.

In step 508 the waveform image is superimposed on the multi-dimensional representation of the welded object 100. In this regard reference point $l_0$, may be used as a basis for aligning the waveform image of the propagated energy on to the multi-dimensional representation of the welded object 100.

Figure 6:
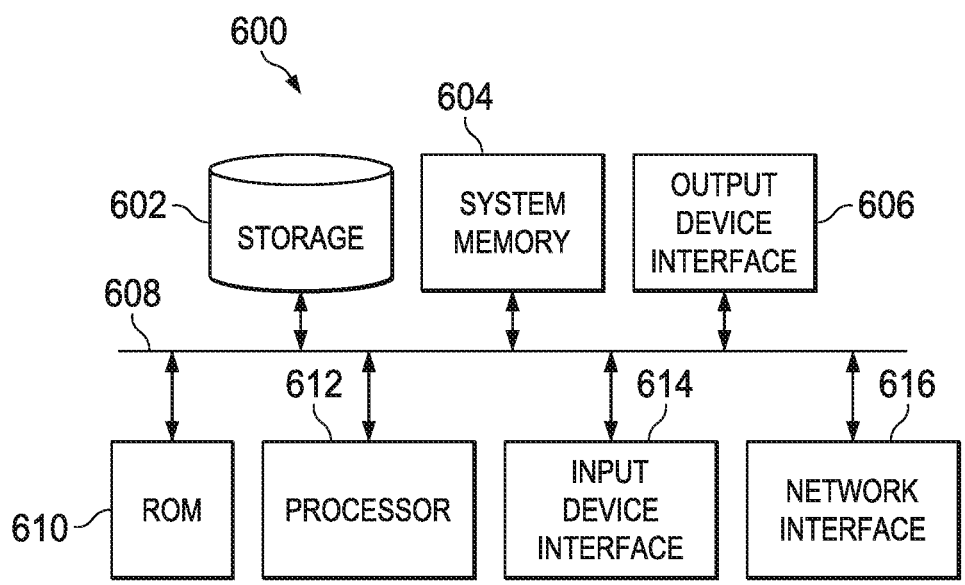
FIG. 6 is a block diagram of an exemplary computer system in which embodiments of the present disclosure may be implemented.

FIG. 6 is a block diagram of an exemplary computer system 600 in which embodiments of the present disclosure may be implemented. For example, the components of system 300 of FIG. 3A in addition to the steps of method 400 of FIG. 4 and/or method 500 of FIG. 5, as described above, may be implemented using system 600. System 600 can be a computer, phone, PDA, or any other type of electronic device. Such an electronic device includes various types of computer readable media and interfaces for various other types of computer readable media. As shown in FIG. 5, system 600 includes a permanent storage device 602, a system memory 604, an output device interface 606, a system communications bus 608, a read-only memory (ROM) 610, processing unit(s) 612, an input device interface 614, and a network interface 616.

Bus 608 collectively represents all system, peripheral, and chipset buses that communicatively connect the numerous internal devices of system 600. For instance, bus 608 communicatively connects processing unit(s) 612 with ROM 610, system memory 604, and permanent storage device 602.

From these various memory units, processing unit(s) 612 retrieves instructions to execute and data to process in order to execute the processes of the subject disclosure. The processing unit(s) can be a single processor or a multi-core processor in different implementations.

ROM 610 stores static data and instructions that are needed by processing unit(s) 612 and other modules of system 600. Permanent storage device 602, on the other hand, is a read-and-write memory device. This device is a non-volatile memory unit that stores instructions and data even when system 600 is off. Some implementations of the subject disclosure use a mass-storage device (such as a magnetic or optical disk and its corresponding disk drive) as permanent storage device 602.

Other implementations use a removable storage device (such as a floppy disk, flash drive, and its corresponding disk drive) as permanent storage device 602. Like permanent storage device 602, system memory 604 is a read-and-write memory device. However, unlike storage device 602, system memory 604 is a volatile read-and-write memory, such a random access memory. System memory 604 stores some of the instructions and data that the processor needs at runtime. In some implementations, the processes of the subject disclosure are stored in system memory 604, permanent storage device 602, and/or ROM 610. For example, the various memory units include instructions for computer aided pipe string design based on existing string designs in accordance with some implementations. From these various memory units, processing unit(s) 612 retrieves instructions to execute and data to process in order to execute the processes of some implementations.

Bus 608 also connects to input and output device interfaces 614 and 606. Input device interface 614 enables the communication of information and selection of commands to the system 600. Input devices used with input device interface 614 include, for example, alphanumeric, QWERTY, or T9 keyboards, microphones, and pointing devices (also called "cursor control devices"). Output device interfaces 606 enables, for example, the display of images generated by the system 600. Output devices used with output device interface 606 include, for example, printers and display devices, such as cathode ray tubes (CRT) or liquid crystal displays (LCD). Some implementations include devices such as a touchscreen that functions as both input and output devices. It should be appreciated that embodiments of the present disclosure may be implemented using a computer including any of various types of input and output devices 341 for enabling interaction with a user. Such interaction may include feedback to or from the user in different forms of sensory feedback including, but not limited to, visual feedback, auditory feedback, or tactile feedback. Further, input can be received in any form including, but not limited to, acoustic, speech, or tactile input. Additionally, interaction with the input device 614 may include transmitting and receiving different types of information, e.g., in the form of documents, to and from the input device 614 via the above-described interfaces.

Also, as shown in FIG. 6, bus 608 also couples system 600 to a public or private network (not shown) or combination of networks through a network interface 616. Such a network may include, for example, a local area network ("LAN"), such as an Intranet, or a wide area network ("WAN"), such as the Internet. Any or all components of system 600 can be used in conjunction with the subject disclosure.

These functions described above can be implemented in digital electronic circuitry, in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself. Accordingly, the steps of method 400 of FIG. 4 and/or method 500 of FIG. 5, as described above, may be implemented using system 300 or any computer system having processing circuitry or a computer program product including instructions stored therein, which, when executed by at least one processor, causes the processor to perform functions relating to these methods.

As used in this specification and any claims of this application, the terms "computer", "server", "processor", and "memory" all refer to electronic or other technological devices. These terms exclude people or groups of people. As used herein, the terms "computer readable medium" and "computer readable media" refer generally to tangible, physical, and non-transitory electronic storage mediums that store information in a form that is readable by a computer.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., a web page) to a client device (e.g., for purposes of displaying data to and receiving input from a (I/O) device 341 interacting with the client device). Data generated at the client device (e.g., a result of the (I/O) device 341 interaction) can be received from the client device at the server.

It is understood that any specific order or hierarchy of steps in the processes disclosed is an illustration of exemplary approaches. Based upon design preferences, it is understood that the specific order or hierarchy of steps in the processes may be rearranged, or that all illustrated steps be performed. Some of the steps may be performed simultaneously. For example, in certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Furthermore, the exemplary methodologies described herein may be implemented by a system including processing circuitry or a computer program product including instructions which, when executed by at least one processor, causes the processor to perform any of the methodology described herein.

Thus, a computer implemented method for the graphical representation and data presentation of weld inspection results has been described herein, wherein the method includes obtaining an ultrasound image and phased array ultrasonic testing (PAUT) inspection data from a PAUT inspection of the welded object, creating a multi-dimensional representation of the welded object; and superimposing the ultrasound image onto the multi-dimensional representation of the welded object.

For the foregoing embodiment, the method may include any of the following steps alone or in combination with each other:

Propagating an acoustical signal through each welded joint during the PAUT inspection and displaying at least three reflections.

Creating a three-dimensional representation of the welded object.

Obtaining a plurality of ultrasound images and phased array ultrasonic testing (PAUT) inspection data from a PAUT inspection and grouping the plurality of ultrasound images and the PAUT inspection data from the PAUT inspection by weld size, weld layout or weld type.

Determining whether the plurality of ultrasound images and PAUT inspection data from the PAUT inspection are improperly grouped with respect to weld size, weld layout or weld type.

Including a reference point on the welded object that correlates to a reference point on the multi-dimensional representation.

Obtaining spatial and magnitude information of a flaw from the PAUT inspection of the welded object.

Obtaining information related to equipment used during the PAUT inspection of the welded object.

Obtaining information related to the calibration of the PAUT inspection.

Obtaining information related to welding design parameters of the plurality of welded joints and the welded object.

Determining whether a flaw has been identified in each welded joint.

Presenting a listing of welded joints in which flaws have been identified and the plurality of ultrasound images related to a selected welded joint using a graphical user interface via a display of a computing device.

Selecting an image from the plurality of exported ultrasound images to create the multi-dimensional representation of the PAUT inspected welded object.

Creating a multi-dimensional representation of the PAUT inspected welded joint by:

transforming a selected image from the plurality of exported ultrasound images into the shape of the representative image of the welded joint;

obtaining a multi-dimensional digital copy of the representative image of the welded joint; and superimposing the selected image from the exported ultrasound images on to the representative image of the welded joint.

Merging the multi-dimensional representation of the PAUT inspected welded joint, user selected PAUT inspection data from the PAUT inspection and the ultrasound image into an evaluation report for each welded joint.

Merging the multi-dimensional representation of the welded joint, the user selected PAUT inspection data from the PAUT inspection and the exported ultrasound images into an evaluation report for each welded joint by:

providing a database template to designate a display location of the 3-D representation of the welded joint, the user selected PAUT inspection data from the PAUT inspection and the exported ultrasound images for each welded joint for each welded joint in the evaluation report; and placing the extracted 3-D representation of the welded joint, the user selected PAUT inspection data from the PAUT inspection and the exported ultrasound images into the designated display locations within the database template for presentation within the evaluation report for each welded joint.

Merging the evaluation report for each welded joint within the plurality of welded joint within the welded object into a master report.

Merging the evaluation report for each welded joint with the plurality of welded joints of the welded object into a master report further comprises importing the phased array ultrasonic testing (PAUT) inspection data from a PAUT inspection into the master report.

Additionally an alternate embodiment of a computer implemented method for the graphical representation and data presentation of weld inspection results has been described herein, wherein the method includes propagating energy into a welded joint of an object, obtaining a waveform image of the propagated energy, identifying a multi-dimensional representation of the object, and superimposing the waveform image onto the multi-dimensional representation of the object.

For the foregoing embodiment, the method may include any of the following steps alone or in combination with each other:

Propagating acoustic energy through the object.

Creating a three dimensional image of the multi-dimensional representation.

Identifying a reference point on the object; propagating energy into the welded joint at distinct locations along the surface of the object relative to the reference point; and superimposing the waveform image on the multi-dimensional object utilizing the reference point.

Selecting a multi-dimensional representation that has the same shape as the object and attributing dimensions to the representation that correspond with dimensions of the object.

Selecting the multi-dimensional representation from a library of shapes.

Generating the multi-dimensional representation based on the dimensions of the object.

When the object is a pipe having a circumference with a welded joint extending about a least a portion of the circumference; directing energy into the welded joint from a plurality of spaced locations on the surface of the pipe along the welded joint.

When the object is a pipe having a circumference with a welded joint extending about an entire portion of the circumference; directing energy into the welded joint from a plurality of spaced locations along the entire surface of the pipe along the welded joint.

Additionally a system for the graphical representation and data presentation of weld inspection results has been described. Embodiment of the system may include an external memory and an engine. Other embodiments of the system may generally include an external memory and an engine, the engine including an export module, a transformation module, a merger module, a memory, and a GUI. In other embodiments, the engine and export module may be communicatively coupled to one another via an internal bus of the system. Further, in other embodiments, the engine may be operably and communicatively coupled to a network interface.

For any of the foregoing embodiments, the system for the graphical representation and data presentation of weld inspection results may further include any one of the following elements, alone or in combination with each other:

at least one processor; and a memory coupled to the processor having instructions stored therein, which when executed by the processor, cause the processor to perform functions, including functions to:

obtain a plurality of ultrasound images and phased array ultrasonic testing (PAUT) inspection data from a PAUT inspection of each the plurality of welded joints within the welded object;

group the plurality of ultrasound images and the PAUT inspection data from the PAUT inspection by a predetermined characteristic within a computer readable medium;

export the plurality of ultrasound images and the PAUT inspection data from the PAUT inspection for each welded joint within the plurality of welded joints from the computer readable medium;

create a multi-dimensional representation of a PAUT inspected welded joint for each welded joint within the plurality of welded joints by selecting one of the plurality of exported ultrasound images and superimposing it on to a multi-dimensional representative image of the welded joint;

merge the multi-dimensional representation of the welded joint, user selected PAUT inspection data from the PAUT inspection and the plurality of exported ultrasound images into an evaluation report for each welded joint; and merge the evaluation report for each welded joint within the plurality of welded joints of the welded object into a master report.

A processor which further functions to determine whether an acoustical signal generated during a phased array ultrasonic testing (PAUT) inspection indicates a flaw within each welded joint.

A processor which further functions to export the PAUT inspection data from the PAUT inspection comprising spatial and magnitude information of the flaw if the flaw in the event the processor determines a flaw is present.

A processor which further functions to obtain information related to equipment used during the PAUT inspection from the grouped PAUT inspection data.

A processor which further functions to obtain information related to the calibration of the PAUT inspection from the exported PAUT inspection data.

A processor which further functions to obtain information related to welding design parameters of the plurality of welded joints and the welded object from the exported PAUT inspection data.

A GUI operably connected to the at least one processor, the memory, a display of a computing device, and a user input device coupled to computing device wherein the graphical user interfaces functions to display:

a list of welded joints in which flaws have been identified; and a plurality of ultrasound images related to a selected welded joint.

A GUI which further functions to allow selection of an image from the plurality of exported ultrasound images to create a 3-D representation the PAUT inspected welded joint using the user input device coupled to the computing device.

A processor which further functions to:

transform a selected image from the plurality of exported ultrasound images into the shape of the representative image of the welded joint;

obtain a multi-dimensional digital copy of the representative image of the welded joint; and superimpose the selected image from the plurality of exported ultrasound images on to the representative image of the welded joint;

thereby creating the multi-dimensional representation of the PAUT inspected welded joint.

A processor which further functions to:

use a database template to designate a display location of the multi-dimensional representation of the PAUT inspected welded joint, the user selected PAUT inspection data from the PAUT inspection and the plurality of exported ultrasound images for each welded joint in the evaluation report;

group the multi-dimensional representation of the PAUT inspected welded joint, the user selected PAUT inspection data from the PAUT inspection and the plurality of exported ultrasound images; and place the extracted the multidimensional representation of the PAUT inspected welded joint, the user selected PAUT inspection data from the PAUT inspection and the exported ultrasound images into the designated display locations within the database template for presentation within the evaluation report for each welded joint.

A processor which further functions to import the PAUT inspection data from a PAUT inspection into the master report.

In yet a further embodiment the system for the graphical representation and data presentation of weld inspection results may comprise a computer-readable storage medium having instructions stored therein, which when executed by a computer cause the computer to perform a plurality of functions, including functions to:

obtain a plurality of ultrasound images and phased array ultrasonic testing (PAUT) inspection data from a PAUT inspection of each the plurality of welded joints within a welded object;

group the plurality of ultrasound images and the PAUT inspection data from the PAUT inspection by a predetermined characteristic within a computer readable medium;

export the plurality of ultrasound images and the PAUT inspection data from the PAUT inspection for each welded joint within the plurality of welded joints from the computer readable medium;

create a multi-dimensional representation of a PAUT inspected welded joint for each welded joint within the plurality of welded joints by selecting one of the exported ultrasound images and superimposing it on to a multi-dimensional representative image of the welded joint;

merge the multi-dimensional representation of the PAUT inspected welded joint, user selected PAUT inspection data from the PAUT inspection and the exported ultrasound images into an evaluation report for each welded joint; and merge the evaluation report for each welded joint within the plurality of welded joints of the welded object into a master report.

While specific details about the above embodiments have been described, the above hardware and software descriptions are intended merely as example embodiments and are not intended to limit the structure or implementation of the disclosed embodiments. For instance, although many other internal components of the system 600 are not shown, those of ordinary skill in the art will appreciate that such components and their interconnection are well known.

In addition, certain aspects of the disclosed embodiments, as outlined above, may be embodied in software that is executed using one or more processing units/components. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives, optical or magnetic disks, and the like, which may provide storage at any time for the software programming.

Additionally, the flowchart and block diagrams in the figures illustrate the architecture, functionality, and operation of possible implementations of systems, methods and computer program products according to various embodiments of the present disclosure. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The above specific example embodiments are not intended to limit the scope of the claims. The example embodiments may be modified by including, excluding, or combining one or more features or functions described in the disclosure.

As used herein, the singular forms "a", "an" and "the" are intended to include the plural forms as well, unless the context clearly indicates otherwise. It will be further understood that the terms "comprise" and/or "comprising," when used in this specification and/or the claims, specify the presence of stated features, integers, steps, operations, elements, and/or components, but do not preclude the presence or addition of one or more other features, integers, steps, operations, elements, components, and/or groups thereof. The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the embodiments in the form disclosed. Many modifications and variations will be apparent to those of ordinary skill in the art without departing from the scope and spirit of the disclosure. The illustrative embodiments described herein are provided to explain the principles of the disclosure and the practical application thereof, and to enable others of ordinary skill in the art to understand that the disclosed embodiments may be modified as desired for a particular implementation or use. The scope of the claims is intended to broadly cover the disclosed embodiments and any such modification.

What is claimed is:

1. A computer implemented-method for graphically representing and presenting inspection results of a welded joint of a welded object, the method comprising:

obtaining an ultrasound image and phased array ultrasonic testing (PAUT) inspection data from a PAUT inspection of the welded joint;

creating a multi-dimensional representation of the welded joint; and utilizing the PAUT inspection data to superimpose the ultrasound image onto the multi-dimensional representation of the welded joint.

2. The computer implemented-method of claim 1, further comprising propagating an acoustical signal through each welded joint during the PAUT inspection and displaying at least three reflections.

3. The computer implemented-method of claim 1, wherein the multi-dimensional representation is three dimensional.

4. The computer implemented-method of claim 1, further comprising obtaining a plurality of ultrasound images and PAUT inspection data from a PAUT inspection and grouping the plurality of ultrasound images and the PAUT inspection data from the PAUT inspection by weld size, weld layout or weld type.

5. The computer implemented-method of claim 1, wherein the inspection data includes a reference point on the welded object that correlates to a reference point on the multi-dimensional representation.

6. The computer implemented method of claim 1, further comprising obtaining spatial and magnitude information of a flaw from the PAUT inspection of the welded joint within the welded object.

7. The computer implemented-method of claim 1, further comprising obtaining information related to equipment used during the PAUT inspection of the welded object.

8. The computer implemented-method of claim 1, further comprising obtaining information related to calibrating of PAUT inspection equipment.

9. The computer implemented-method of claim 1, further comprising obtaining information related to welding design parameters of each welded joint within the welded object and the welded object.

10. The computer implemented-method of claim 1, further comprising determining whether a flaw has been identified in each welded joint within the welded object.

11. The computer implemented-method of claim 10, further comprising, via a display of a computing device, presenting a listing of welded joints in which flaws have been identified and a plurality of ultrasound images related to a selected welded joint using a graphical user interface.

12. The computer implemented-method of claim 11, further comprising selecting an image from the plurality of ultrasound images and utilizing the selected image to create the multi-dimensional representation of the PAUT inspected welded joint.

13. The computer implemented-method of claim 1, wherein creating a multi-dimensional representation of the PAUT inspected welded joint further comprises:
    transforming a selected image from the plurality of ultrasound images into a shape of a representative image of the welded joint;
    obtaining a multi-dimensional digital copy of the representative image of the welded joint; and
    superimposing the selected image from the ultrasound images on to the representative image of the welded joint.

14. The computer implemented-method of claim 1, further comprising merging the multi-dimensional representation of the PAUT inspected welded joint, user selected PAUT inspection data from the PAUT inspection and the ultrasound image into an evaluation report for one or more welded joints.

15. The computer implemented-method of claim 14, wherein merging the multi-dimensional representation of the welded joint, the user selected PAUT inspection data from the PAUT inspection and the ultrasound images into an evaluation report for each welded joint further comprises:
    providing a database template to designate a display location of the multi-dimensional representation of the welded joint, the user selected PAUT inspection data from the PAUT inspection and the ultrasound images for each welded joint for each welded joint in the evaluation report; and
    placing the multi-dimensional representation of the welded joint, selected PAUT inspection data from the PAUT inspection and the ultrasound images into the designated display locations within the database template for presentation within the evaluation report for a welded joint.

16. The computer implemented-method of claim 14, further comprising merging the evaluation report for each welded joint within the welded object into a master report.

17. The computer implemented of method claim 16, wherein merging the evaluation report for each welded joint of the welded object into a master report further comprises importing the PAUT inspection data from a PAUT inspection into the master report.

18. The computer implemented-method of claim 1, further comprising rewelding a welded joint determined to contain a flaw.

* * * * *